United States Patent
Dam

[19]

[11] Patent Number: 5,808,200
[45] Date of Patent: Sep. 15, 1998

[54] ULTRASONIC SENSOR WITH CONTINOUS AND DEMAND SELF-TEST FOR LIQUID AND DRY PRODUCT LEVEL MEASUREMENT

[75] Inventor: Naim Dam, Muttontown, N.Y.

[73] Assignee: Cosense, Inc., Hauppauge, N.Y.

[21] Appl. No.: 917,254

[22] Filed: Aug. 25, 1997

[51] Int. Cl.[6] ................................................. G01N 29/02
[52] U.S. Cl. .................... 73/610; 73/861.18; 73/861.25; 73/861.29
[58] Field of Search ........................... 73/861.18, 861.19, 73/861.23, 861.25, 861.26, 861.27, 861.28, 861.29, 610

[56] References Cited

U.S. PATENT DOCUMENTS

| | | | |
|---|---|---|---|
| 5,031,467 | 7/1991 | Rambow | 73/861.25 |
| 5,179,862 | 1/1993 | Lynnworth | 73/861.28 |
| 5,269,188 | 12/1993 | Esin et al. | 73/610 |
| 5,437,178 | 8/1995 | Esin et al. | 73/610 |
| 5,473,948 | 12/1995 | Moss et al. | 73/861.19 |
| 5,503,035 | 4/1996 | Itoh et al. | 73/861.19 |
| 5,663,508 | 9/1997 | Sparks | 73/861.71 |

*Primary Examiner*—Max H. Noori
*Attorney, Agent, or Firm*—Gordon D. Coplein

[57] ABSTRACT

An ultrasonic sensor having a support structure of first and second walls with a gap of fixed distance therebetween. A piezoelectric element for transmitting and receiving ultrasonic energy is bonded to the inner face of one of the walls and the energy transmitted across the gap is reflected from the other wall back to the element. Two timing windows are set, one for the time of energy transmission across the gap with liquid present and the other with the gap being dry. The received energy at the time of the window indicating the dry gap condition is used as a self-test signal to check element dis-bonding. In a sensor with two elements, one bonded to each of the support walls, one element serves as the transmitter and the other as the receiver.

11 Claims, 3 Drawing Sheets

ULTRASONIC SENSOR WITH CONTINOUS AND DEMAND SELF-TEST FOR LIQUID AND DRY PRODUCT LEVEL MEASUREMENT

FIELD OF THE INVENTION

The present invention relates to ultrasonic sensors operating under either or both of air and liquid conditions and a system for the self-test of whether the piezoelectric transducer element used in the sensor is properly bonded to a sensor support wall.

BACKGROUND OF THE INVENTION

Ultrasonic sensors used for measuring the presence of a liquid are well known. One well-known type is called a contact, or invasive, type sensor. This type of sensor utilizes a support structure defining a gap into which the liquid flows. In such sensors, a piezoelectric (crystal) transducer element is bonded by a suitable adhesive, such as an epoxy, to the inner face of one or both walls of the structure forming the gap. The element transmits energy and if there is liquid present in the gap the energy will travel across the gap at a known first velocity of about 1500 meters/second.

In a sensor using one element, energy is transmitted across the gap through the liquid, or air if the gap is dry, to the opposing wall of the support structure from which it is reflected back to the element. Depending upon the size of the gap, detection of the reflected signal at a first time indicates the presence of liquid in the gap. In a typical sensor, if there is no liquid in the gap, the energy will be dissipate in the air and not received back at the transmitting element. In a two element type sensor, there is an element bonded on the inner face of each surface of the opposing walls of the gap defining support structure. Here, the second element receives the energy transmitted across the gap at a time determined by the gap distance and the presence of liquid in the gap.

It is desired to provide such sensors with self-test capability to check, either continuously or on demand, failure of any of the sensor components. This includes the bonding of the piezoelectric element, or elements, to the respective inner face, or faces, of the gap surfaces of the support structure. That is, it is desired to determine if an element has become dis-bonded. If an element has become dis-bonded, the sensor will not operate properly to detect material in the gap. Dis-bonding of an element occurs for a variety of reasons such as dropping of the sensor, rapid temperature changes (thermal shock) and other factors. In effect, dis-bonding of an element causes the sensor to become inoperative.

One arrangement intended to check the integrity of a sensor is disclosed in U.S. Pat. No. 5,269,188 to Esin et al granted Dec. 14, 1993. This patent discloses a frame type sensor support structure in which a stem connects the two gap forming surfaces. In a sensor using two elements, one is bonded to the interior of one of the support structure surfaces forming the gap and serves as a transmitter and the other is bonded to the other surface and serves as a receiver. When energy is transmitted from the transmitter element, a certain amount of it passes, or leaks, directly through the stem part of the sensor support frame connecting the two surfaces forming the gap and is received by the receiver element for use as a self-test signal. This leaked energy does not travel across the gap and it is used as a self-test signal.

A period of time, or time window, for this self-test signal travelling through the support frame to be received by the element mounted to the other surface of the frame gap is set in relation to a time window at which the main energy passing through liquid in the gap, if present, is to be detected. The appearance of a signal in the self-test time window in the dry gap condition is to indicate that the sensor is supposed to be functioning properly. However, this arrangement is not fully capable of checking for dis-bonding of a piezoelectric element, or elements. This is due to the fact that energy can leak out from the back surface or sides of a dis-bonded element and travel through the stem to the receiver element. This situation is sometimes referred to as 'cross-talk' and can occur when the gap is either wet or dry. Cross-talk also can occur in a sensor using only one element in that the part of the energy used for self-test can leak through the stem to the opposing surface for transmission through liquid in the gap back to the one element and give an indication of the sensor operating properly or not.

In the inventor's U.S. Pat. No. 5,663,503, titled "Invasive and Non-Invasive Ultrasonic Sensor With Continuous and Demand Self-Test", granted on Sep. 2, 1997, self-test of dis-bonding of an element is accomplished by measuring the round trip travel time of an ultrasonic energy signal from the front face of the piezoelectric element to the interface of the wall of the support structure to which it is bonded and the air or liquid interface of the gap with the support wall. This arrangement to operate properly should use a highly damped crystal, which is relatively costly, and the detection circuitry can be relatively complicated.

BRIEF DESCRIPTION OF THE INVENTION

In accordance with the invention, an ultrasonic gap type sensor with a gap of a known distance has a piezoelectric element for transmitting and receiving ultrasonic energy bonded by an adhesive to a surface of the support structure that defines the gap. When such a structure having a single element is operated in an energy transmitting mode, the energy transmitted by the element is reflected from the opposing surface of the gap support structure. When the sensor is in a receiving mode, the different times of arrival of the reflected signal can be predicted for each of the cases of the gap being wet or dry. The received energy at these two different times is used as a self-test signal to check element dis-bonding with the travel time in the dry gap condition being fully determinative of dis-bonding. If the element is totally dis-bonded or partially dis-bonded, no reflected signal will be received at each of the known times. With the element being properly bonded, the signal will be received when the gap is dry. Detection of a dis-bonded element is accomplished for conditions of the gap being either wet or dry, which can be an operating condition for the sensor in a vessel in which the liquid level varies. In the present invention, the integrity of the sensor is checked during the changing wet and dry gap conditions, whereas prior art sensors would not check sensor integrity when the gap is dry.

In a preferred embodiment of the invention a window is set to detect reception of the energy reflected from the opposing surface of the support wall for each of the dry and wet conditions of the gap. The timing of each window can be set since the round trip time of the energy transmitted from the element across the gap under both wet and dry conditions is known with a fair degree of precision. In a properly operating sensor in which the element is not dis-bonded, the reflected signal will be received at the time of occurrence of both of the windows when the gap is wet and at the longer occurring time of the window for the dry gap condition. If the sensor is inoperative, no signal will be received in either of the wet or dry windows. Also, no return signal will be received in either window if the sensor gap is filled with dry products, such as fly ash, sawdust and light powder, meaning that the sensor is inoperative.

For a gap type sensor using two elements, windows for the wet and dry gap conditions are set for only a one way trip of the energy since the energy from the transmitting element is received by the receiving element on the other side of the gap.

The sensor and electronic detection circuitry of the invention are relatively simple to manufacture.

OBJECTS OF THE INVENTION

It is an object of the invention to provide for a sensor with capability of continuous or demand self-test of the integrity of an ultrasonic sensor relative to dis-bonding of its piezoelectric element, or elements, from a part of the sensor support structure under both wet and dry gap conditions.

Another object is to provide a self-testing ultrasonic gap type sensor that checks either on demand or continuously the integrity of the bonding of the piezoelectric transducer element, or elements, to the sensor support structure by measuring the transmission time of the energy across the gap under both dry and wet gap conditions with measurement of dry gap transmission used to detect element dis-bonding or other malfunction.

Yet another object is to provide an ultrasonic gap type sensor with self-test capability in which signals transmitted and received by the sensor across the gap of known distance under both wet and dry conditions are checked for occurrence at predetermined times.

Still a further object is to provide a sensor in which there is a self-test of element dis-bonding that operates continuously or on demand under dry conditions of the sensor gap.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
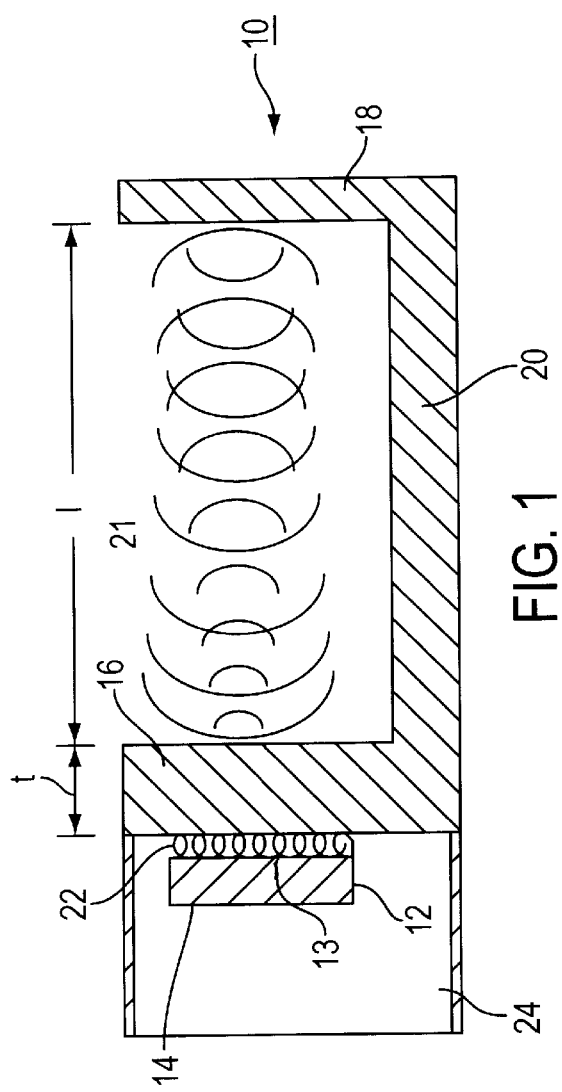
FIG. 1 is a cross-sectional view of a typical sensor showing mounting of its components.

FIG. 1 show details of a gap type sensor 10 having a single piezoelectric crystal transducer element 12. The sensor includes a support structure having a first end wall 16 of thickness 't' and a second end wall 18 joined by a stem 20 defining a gap 21 of distance 'l' between the opposing faces of the support walls 16, 18. The sensor support walls 16, 18 can be of any desired shape, such as circular, and the connecting stem 20 of arcuate, circular or other suitable shape. The support structure can be made of any suitable material, for example, stainless steel, MONEL, HASTALLOY-C/B, aluminum, titanium, CPVC, PVC, KYNAR, TEFLON and Carpenter-20. Any suitable material compatible with the sensor environment can be used.

The element 12 is a relatively thin disk of piezoelectric material, such as PZT and preferably of PVDF type, a flexible plastic material made by AMP of Harrisburg, Pa., and can be of circular or rectangular shape. An electrode (not shown) is plated on each face of the element 12 and a lead wire (also not shown) is connected to each electrode to provide connection between the element and a source of exciting energy and/or to receiving circuits, as described below. The thickness of the element is generally about one-half wavelength of the sensor operating frequency.

In a typical sensor, one face 13 of the element, the one bonded to the support wall 16, is covered with a coating of an abrasion resistant material 22, such as epoxy, of a thickness of approximately one-fourth wavelength of the element operating frequency to bond the element to the support wall. It is preferred that the epoxy be of a type that has an impedance substantially equal to air at the operating frequency of the element. The other element face 14 is covered with one or more layers of a backing material 24, such as epoxy, to absorb acoustic energy produced by the element when excited so as to prevent this energy from returning via the rest of the support structure to the element.

As shown in FIG. 1, energy from element 12, when excited, is transmitted through the thickness t of the support wall 16 to the interface with the gap 21. If a liquid is present in the gap 21, that is, the gap is wet, the energy from the transmitting element 12 travels across the gap 21, is reflected from the opposing face of the other support wall 18 back to and through the support wall 16 to the element 12 which now acts as a receiving element. The velocity of the acoustic energy with a liquid, such as water, in the gap 21 is about 1500 meters/second for water at room temperature. The distances of the thickness of the epoxy bonding material 22, the support wall 16 distance t and the gap distance l are known. In a transducer with a gap 21 distance of one inch, the travel time for the energy when the gap is wet with water is about 33 microseconds. Other liquids with which typical sensors are used have acoustic energy velocities of from about 900 meters/second to about 2200 meters/sec.

When the gap 21 is dry, that is, there is no liquid, the acoustic energy travels the same round trip route from element 12, but at a lower velocity, and is somewhat attenuated. The invention makes use of the fact that ultrasonic energy at he proper frequency will travel across an air gap if the gap is small enough. The velocity of the acoustic energy in air at room temperature is 343 meters/second and the travel time approximately 147 microseconds. As seen, there is a substantial difference between the travel time of the ultrasonic energy under the conditions of the gap being wet with most types of liquids and being dry.

As discussed above, element 12 is subject to dis-bonding from support wall 16 due to a variety of reasons. In the present invention, the round trip time difference between ultrasonic energy travel in a liquid and in air is used as a self-test to detect improper operation of the sensor such as would be caused by dis-bonding of the element 12 from the support wall 16.

Figure 2:
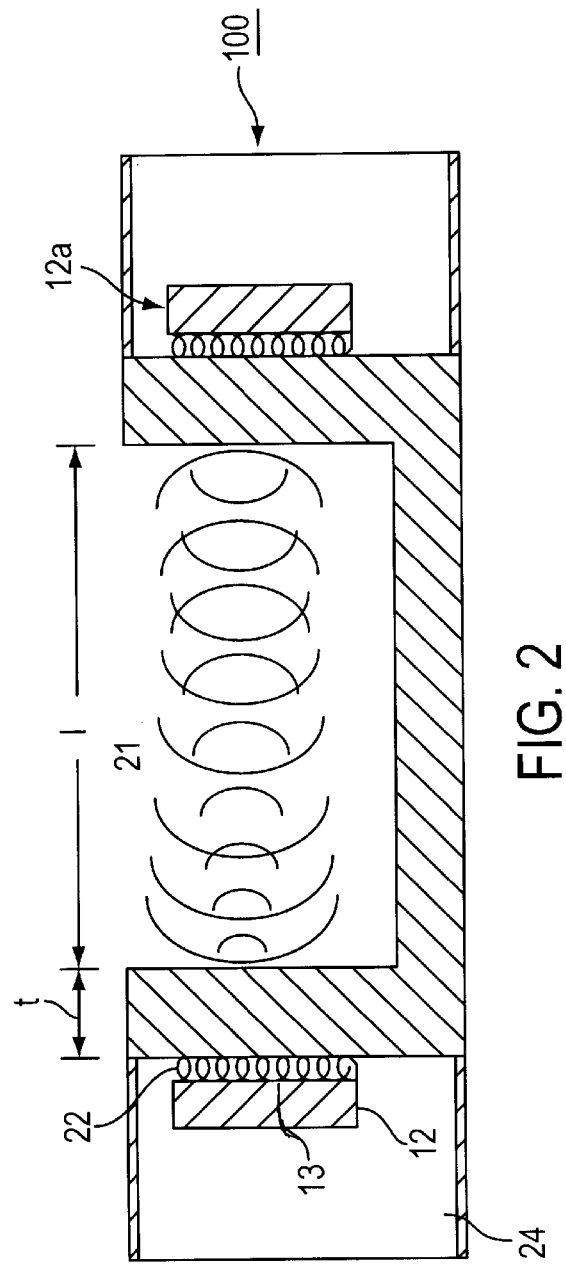
FIG. 2 is a cross-sectional view of a sensor using two piezoelectric elements.

FIG. 2 shows another embodiment of a sensor 100 similar to that of FIG. 1 in which two elements 12 and 12a are used. The same reference numbers are used for the same elements. Here the second element 12a is mounted in a manner similar to the first element 12, as described with respect to FIG. 1, to the second wall 18 of the sensor support structure. Connecting wires (not shown) pass through and are embedded in the support stem 20 for connection to the electrodes on the element 12a. In FIG. 2, element 12 is used as a transmitter and element 12a as a receiver. That is, the energy from transmitter element 12 is not reflected from the opposing face of support wall 18 but is instead received by the element 12a. The transmitter and receiving functions of elements 12 and 12a can be interchanged.

In FIG. 2, the receiver element 12a is subject to the same type of dis-bonding problems described above as element 12. As described below, the present invention also provides a dis-bonding self-test for both elements 12 and 12a of a two element type sensor by alternately using each element in a transmitting mode.

With respect to the sensors of FIGS. 1 and 2, the following energy round trip travel time relations, ignoring the support end wall 16 distance t and the thickness distance of the epoxy 22, exist:

(1) for a one element sensor (FIG. 1);

$$T_s=2l/V_l \text{ and } T_s=2l/V_a$$

(2) for a dual element sensor (FIG. 2);

$$T_d=l/V_l \text{ and } T_d=l/V_a$$

where, l is the distance between the signal transmitting element and the reflector (or second) receiving element, $V_l$ is the velocity of the acoustic energy in liquid in the gap 21, $V_a$ is the velocity of the acoustic energy in air in the gap 21, $T_s$ is the round trip arrival time in a single element sensor, and $T_d$ is the arrival time in a dual element sensor.

Figure 3:
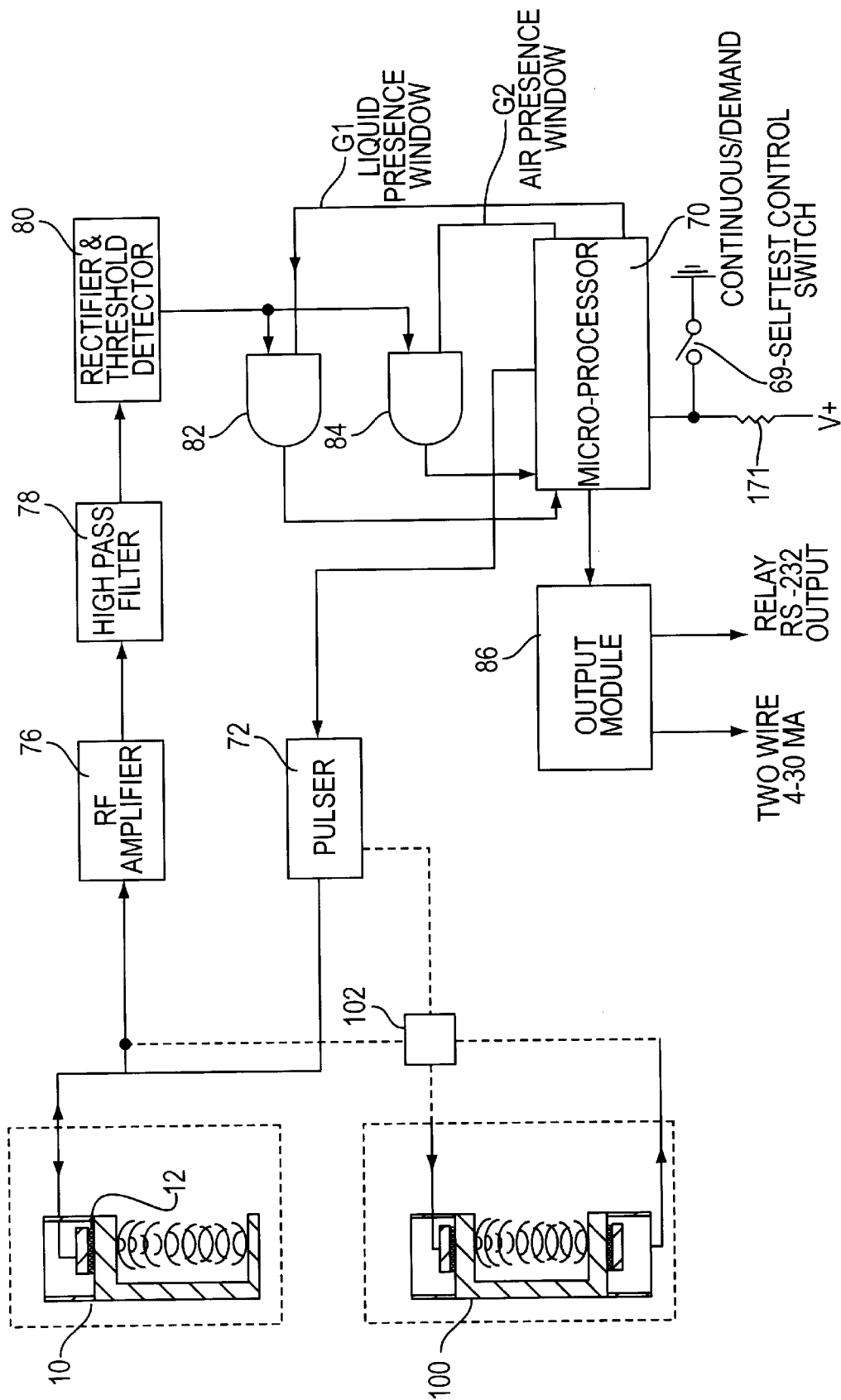
FIG. 3 is a schematic block diagram of a first embodiment of a circuit for a sensor with continuous or demand self-test capability.
Figure 4:
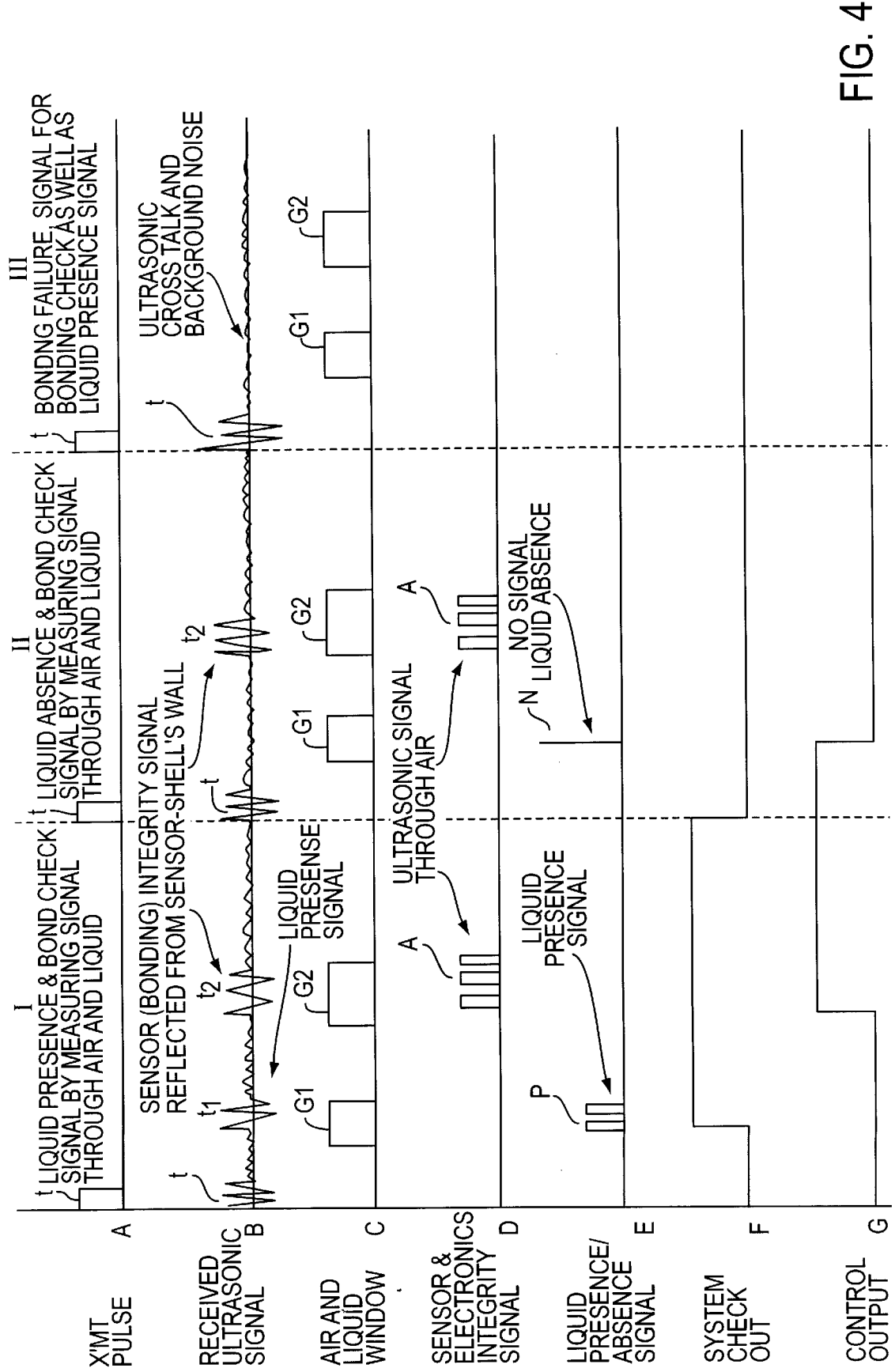
FIG. 4 is a timing diagram related to the circuit of FIG. 3.

FIGS. 3 and 4 show a preferred embodiment of the invention that utilizes a signal window technique to check the integrity of the bonding of the sensor element(s) on a self-test basis. FIG. 3 is a circuit diagram of the electronic components and FIG. 4 shows the signal timing diagram. FIG. 4 is divided across its width into three sections illustrating three different conditions, these being:

I—piezoelectric element bond OK and liquid in the sensor gap,

II—element bond OK and no liquid is in the sensor gap, and

III—bonding failure (element dis-bonded) and liquid is present in the sensor gap.

The circuit of FIG. 3 includes, as shown in the upper left corner of the drawing, the single element sensor 10 of FIG. 1, with the element 12 bonded to the wall of the part 16 of the support forming the gap. A programmable microprocessor 70 receives its supply voltage from a suitable voltage source (not shown) through a resistor 71. Microprocessor 70 controls a pulser 72 that repetitively produces a pulse, or burst of pulses, at timed intervals as controlled by the microprocessor. This pulse, t as shown in FIG. 4, is supplied to the sensor element 12 for transmission across the sensor gap, as shown on line A of FIG. 4. In a preferred embodiment of the invention where the sensor gap 21 is about one inch, the frequency of the ultrasonic energy signal t is about 1–2 Mhz.

After the signal t is transmitted by element 12 the microprocessor 70 then sets the circuit to be in the receive mode. The circuit remains in the receive mode until the microprocessor later controls production of the next pulse from the pulser 72 for transmission. With the circuit of FIG. 3 in the receive mode, the transmitted signals that are received after reflection from the support wall 18 after traveling through the wet or dry gap 21 are applied to an RF amplifier 76, preferably of a high gain type. The signal amplified by RF amplifier 76 is applied to the input of a high pass filter 80 and then to a threshold amplifier 82 which passes signals above a predetermined amplitude level.

Microprocessor 70 set two timing gate window signals, as shown on line C of FIG. 4. The first, designated G1, is at a time equal to the round trip travel time of the transmitted pulse t in the sensor gap 21 when there is liquid present. The second window, designated G2, is at a time equal to the round trip travel time of the transmitted pulse t through air when there is no liquid present in sensor gap 21. Window G2 is at a time later than window G1 since the travel time of the pulse t in air (no liquid) is longer than that if there is liquid present in gap 21. The times for the window signals G1 and G2 can be accurately set since the distance of the sensor gap 21 is known and the velocity of the signal t in air and liquid also is known.

The window signal G1 from microprocessor 70 is applied to one input of an AND gate 82 while the window signal G2 is applied to one input of an AND gate 84. The second input to each of the AND gates 82, 84 is from the output of the threshold detector 80. The output of each of the AND gates 82 and 84 is applied to the microprocessor 70. Upon receiving a signal from either of the AND gates, the microprocessor produces a signal to actuate an output module 86. The output module 86 produces an indication of the various signals A, N and P described below. This indication can be a conventional RS 232 output or a current output. These signal indications can activate or drive other devices such as alarms, control lights, etc.

To explain the operation of the circuit of FIG. 3, consider first the case that the element 12 is properly bonded to the wall 16 of the sensor support. As shown in line A of each of sections I, II and III of FIG. 4, the signal t from pulser 72 is transmitted through the support wall 16. Consider sections I and II in which the element 12 is properly bonded to the sensor wall 16. With no liquid present in gap 21, as shown on line B of section II, the signal t will be reflected from the opposing sensor wall 18 and be detected at threshold detector 80 for application to the microprocessor at the time of the window signal G2. As shown on line D, this causes the microprocessor to produce a signal A which indicates that the element 12 is properly operating and that there is no liquid in gap 21. This is the signal used to check the sensor element 12 bonding integrity. The microprocessor 70 also can be configured to produce a signal N as shown on line E that there is no liquid present in the gap. That is, a signal N can be produced even with no liquid in sensor gap 21 so long as the sensor 10 is operating properly, that is, element 12 is properly bonded.

If there is liquid in the sensor gap 21, as shown in section I, there is a reflected signal t1 received by amplifier 76. This is applied from detector 78 at the time of the window signal G1 causing a liquid presence signal P to be produced by microprocessor 70, as shown on FIG. 4, line E of section I. Section I also shows the case of the liquid absence (dry gap) signal A being produced. As indicated above, the gap can vary between being wet or dry.

Section III of FIG. 4 shows the situation where the element 12 is dis-bonded or the sensor 10 is otherwise operating improperly. As seen on line E, neither signal A or P is produced. This means that the sensor 10 is defective.

Line F of FIG. 4 shows that the output module 86 has an output that stays on for so long as there is liquid in the sensor gap. If the gap becomes dry, the signal on line F terminates. Line G of FIG. 4 shows an output from module 86 when there is no liquid in the sensor gap but the signal A through the air in the gap is present, meaning that the sensor is operating properly. The signal on line G stays on until an N signal, indicating no liquid in the gap is received and then goes on again when the next A (dry gap) signal is produced. The signals on lines F and G can be visually indicated or produce different types of sounds.

In a typical application, the microprocessor 70 can have an internal clock operating at 10 MHz and the signal produced by pulser 72 to be transmitted by the sensor is illustratively in the range from 1–2 MHz. With the 10 MHz microprocessor clock frequency, the cycle time, or sampling frequency, allotted for transmission of the signal and its reception can illustratively be 100 milliseconds.

FIG. 3 also shows a switch 69 connected to a port of the microprocessor 70 to set the self-test to either demand or continuous mode. If set to the demand mode, a remotely locate switch can be used to actuate the self-test on demand. In an on demand configuration the microprocessor can be programmed to determine and process the A, N and P signals for a few cycles and then return to normal operation.

The circuit of FIG. 3 can be used with a two element sensor 100 such as shown in FIG. 2. Such a sensor is shown in the lower left part of FIG. 3 and the connections to the circuit by the dotted lines. As explained above, in sensor 100 one element 12 usually serves as the transmitter and the other element 12a as the receiver. To be able to check both elements for dis-bonding, a mode switch 102 is provided. Switch 102 is shown in mechanical analog form but can be implemented by an electronic switching circuit. Here, the microprocessor 70 is programmed to control mode switch 102 to switch the functions of elements 12 and 12a from transmitting to receiving and the circuit connections from the pulser 72 to the RF amplifier 76. When this is done, each element alternately serves as a transmitter and is checked in the manner described above. Here, however, the signals A and P are produced upon receipt across the gap of the transmitted signal by the element which is connected as a receiver element. With the two element sensor, the travel time of the signal t and the production of the window signals G1 and G2 would be half of that needed for the sensor 10 of FIG. 1.

We claim:

1. An ultrasonic sensor comprising:
   a support structure having first and second walls with a gap of fixed distance therebetween;
   an element for transmitting and receiving an ultrasonic energy signal bonded to one face of one of said first and second walls;
   a transmitter for periodically supplying said ultrasonic energy signal to said element to be transmitted through said one wall across said gap to the other of said first and second walls, the dimension of the gap and the frequency of the ultrasonic energy signal being such as to effect transmission of the ultrasonic energy signal from said element across said gap in a dry condition to said other wall;
   a receiver to detect reception of an ultrasonic energy signal received at the other of said first and second walls; and
   a timing circuit setting two window periods for reception of said ultrasonic energy signal by said receiver at respective times corresponding to said gap being dry and said gap being filled with liquid, absence of receipt of a signal at the time of the window period for the gap being dry being indicative of sensor failure.

2. An ultrasonic sensor as in claim 1 further comprising an indicator for producing a signal corresponding to a received energy signal occurring at the time of each said window.

3. An ultrasonic sensor as in claim 2 wherein said indicator further indicates the failure of an ultrasonic energy signal being received corresponding to said element not being properly bonded to said one wall.

4. An ultrasonic sensor as in claim 1 further comprising an indicator that indicates an ultrasonic energy signal being received when the gap is dry corresponding to said element being properly bonded to said one wall.

5. An ultrasonic sensor as in claim 1 wherein said gap has a dimension not greater than one inch.

6. An ultrasonic sensor as in claim 5 wherein the frequency of the ultrasonic energy signal is at least about 1 Mhz.

7. An ultrasonic sensor as in claim 1 wherein a said element is bonded to each said wall, one such element for transmitting said ultrasonic energy signal across said gap and the other said element for receiving said ultrasonic energy signal.

8. An ultrasonic sensor as in claim 1 wherein a said element bonded to said one wall receives the ultrasonic energy signal reflected from the other wall back across the dry gap.

9. An ultrasonic sensor comprising:
   a support structure having first and second walls with a gap of fixed distance therebetween;
   an element for transmitting and receiving an ultrasonic energy signal bonded to one face of one of said first and second walls;
   a transmitter for periodically supplying said ultrasonic energy signal to said element to be transmitted through said one wall across said gap to the other of said first and second walls, the dimension of the gap and the frequency of the ultrasonic energy signal being such as to effect transmission of the ultrasonic energy signal from said element across said gap in a dry condition to said other wall;
   a receiver to detect reception of an ultrasonic energy signal received by the other of said first and second walls after transmission across the dry gap;
   a timing circuit setting a period for reception of the transmitted ultrasonic energy signal at a time corresponding to said gap being dry, absence of receipt of a signal during said period being dry being indicative of sensor failure.

10. An ultrasonic sensor as in claim 9 wherein a said element is bonded to each said wall, one such element for transmitting said ultrasonic energy signal across said gap and the other said element for receiving said ultrasonic energy signal transmitted across the dry gap.

11. An ultrasonic sensor as in claim 9 wherein a said element bonded to one wall receives the ultrasonic energy signal reflected from the other wall back across the dry gap.

* * * * *